United States Patent [19]

Trelles

[11] Patent Number: 5,522,813
[45] Date of Patent: Jun. 4, 1996

[54] METHOD OF TREATING VEINS

[75] Inventor: Mario A. Trelles, Tarragona, Spain

[73] Assignee: Coherent, Inc., Santa Clara, Calif.

[21] Appl. No.: 310,869

[22] Filed: Sep. 23, 1994

[51] Int. Cl.$^6$ .................................................... A61B 17/36
[52] U.S. Cl. ................................. 606/2; 606/9; 606/11; 607/89
[58] Field of Search ......................... 606/9, 2, 10, 11, 606/12, 19, 187; 607/88, 89

[56] References Cited

U.S. PATENT DOCUMENTS

| | | | |
|---|---|---|---|
| 5,000,752 | 3/1991 | Hoskin et al. | 606/9 |
| 5,025,446 | 6/1991 | Kuizenga | 372/21 |
| 5,217,455 | 6/1993 | Tan | 606/9 |
| 5,282,797 | 2/1994 | Chess | 606/9 |
| 5,287,380 | 2/1994 | Hsia | 372/69 |
| 5,290,273 | 3/1994 | Tan | 606/9 |
| 5,304,170 | 4/1994 | Green | 606/9 |
| 5,312,395 | 5/1994 | Tan et al. | 606/9 |
| 5,312,396 | 5/1994 | Feld et al. | 606/11 |
| 5,336,217 | 8/1994 | Buys et al. | 606/9 |
| 5,342,352 | 8/1994 | Franken et al. | 606/9 |
| 5,344,418 | 9/1994 | Ghaffari | 606/9 |
| 5,397,327 | 3/1995 | Koop et al. | 606/17 |

FOREIGN PATENT DOCUMENTS

| | | | |
|---|---|---|---|
| 0172490 | 2/1986 | European Pat. Off. | 606/9 |
| WO90/12545 | 11/1990 | WIPO | A61B 17/36 |
| WO91/13652 | 9/1991 | WIPO | A61N 5/06 |

*Primary Examiner*—Stephen C. Pellegrino
*Assistant Examiner*—Sonya Harris-Ogugua
*Attorney, Agent, or Firm*—Limbach & Limbach; Michael A. Stallman

[57] ABSTRACT

A method of treating vascular lesions is disclosed which includes using a focused beam from a high energy, carbon dioxide laser to irradiate a spot on the surface of the skin over the vessel to be treated. The carbon dioxide output wavelength is highly absorbed by the tissue. By using short, high energy pulses, a small volume of skin can be vaporized or ablated with each pulse with little thermal damage beyond the ablated region. Using multiple pulses, a small channel is drilled in the skin until the vessel is reached. The laser energy absorbed by the blood in the vessel will cause it to coagulate and collapse. This procedure is then repeated at multiple sites along the length of the vessel so that it will collapse and no longer carry any blood.

7 Claims, 1 Drawing Sheet

５,522,813

METHOD OF TREATING VEINS

TECHNICAL FIELD

The subject invention relates to an improved method for the laser treatment of veins.

BACKGROUND OF THE INVENTION

There has been significant interest in developing laser systems which can be used to treat various forms of vascular lesions. The type of vascular disorders that have been investigated include port wine stains, face veins, telangiectasis, and birth marks. A wide variety of medical laser systems have been proposed and introduced to treat these various disorders.

In most prior systems, the laser light is used to irradiate the surface of the skin. The laser energy passes through the tissue and is preferentially absorbed in the blood in the vessel. The energy which is absorbed in the blood, causes the vessel to coagulate and collapse.

Unfortunately, there are problems associated with these systems. More specifically, although most of the energy of the laser beam passes through the tissue to the vessel, scattering and absorption of the light take place in the tissue. This absorption can cause significant changes in skin coloration and even scarring. This problem is even more acute when attempts are made to treat large veins where much higher laser powers are necessary.

Accordingly, it would be desirable to develop an alternative laser treatment method for treating veins which does not have the drawbacks associated with the prior art approaches.

SUMMARY OF THE INVENTION

In accordance with the method of the subject invention, the surface of the skin above the vein is irradiated with a focused laser beam having a wavelength which is directly absorbed by the tissue. The character of the laser energy is selected so that the tissue is rapidly vaporized or ablated with minimal thermal damage to the surrounding tissue. Using this approach, a hole is drilled through the tissue to a depth which reaches the vessel to be treated. The laser light is then used to puncture the vessel, causing coagulation and the ultimate collapse of the vessel.

In the preferred embodiment, the laser energy is supplied by a high power carbon dioxide laser having a emission wavelength in the far infrared. This wavelength (which is 10.6 microns for standard carbon dioxide) is highly absorbed in the water molecules of the tissue. It has been shown that if the radiation is delivered in short pulses, for example, one millisecond or less, the heat will not have time to flow away from the treatment zone and thermal damage will be minimized. Rather, only the tissue exposed to the radiation will be vaporized allowing a hole to be drilled with little thermal damage. The diameter of drilled holes can be kept quite small, on the order of 0.1 to 0.2 mm.

In order to fully treat a vein, it is necessary to drill a number of holes along the length thereof. The process of coagulation and collapse of the vein can be aided by compressing the tissue surrounding the vein.

Since the holes drilled by the laser are quite narrow, the likelihood of coloration changes and scarring associated with the prior art thermal processes is minimized.

Further objects and advantages of the subject invention will become apparent from the following detailed description taken in conjunction with the drawings in which:

DETAILED DESCRIPTION OF THE PREFERRED EMBODIMENT

Figure 1:
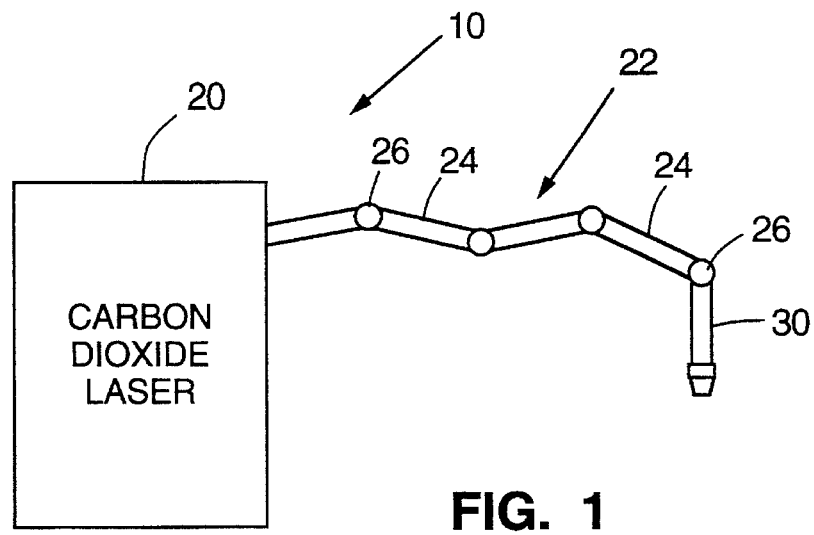
FIG. 1 illustrates a laser system and delivery device for use in the method of the subject invention.

Referring to FIG. 1, there is illustrated a laser system 10 for performing the method of the subject invention. The laser system includes a carbon dioxide laser 20 for generating a far infrared beam which is highly absorbed in the tissue. Initial experiments with this method were performed with an Ultrapulse carbon dioxide medical laser system from Coherent, Inc. The Ultrapulse laser system includes a RF excited, slab waveguide laser of the type described in U.S. Pat. No. 5,123,028, issued Jun. 16, 1992, and incorporated herein by reference.

The slab waveguide laser in the Ultrapulse device is capable of generating high energy pulses of up to one millisecond in length. The energy per pulse is in the range of 100 to 500 millijoules. When standard carbon dioxide is used as the gas fill, the output wavelength of the laser is at 10.6 microns. The Ultrapulse laser is also offered with the $^{13}CO_2$ isotope of carbon dioxide which generates an output wavelength of 11.1 microns. Either of these lasers can be used to perform the subject method.

When these high energy pulses are focused onto the skin, the irradiated tissue is instantly vaporized or ablated. Each pulse removes a fixed amount of tissue. Due to the short absorption length of the laser energy in tissue and short pulses generated, very little heat is able to diffuse beyond the region of the ablated tissue. By this arrangement, substantially char free ablation can be achieved.

The Ultrapulse laser is presently being used for a wide variety of surgical procedures where such char free ablation is desired. In these procedures, the output from the laser 20 is delivered to the treatment site via an articulated arm 22. The arm 22 includes a plurality of segments 24 interconnected by a series of knuckles 26. Each knuckle includes a set of turning mirrors (not shown) and permits relative rotation between the associated segments 24.

Figure 2:
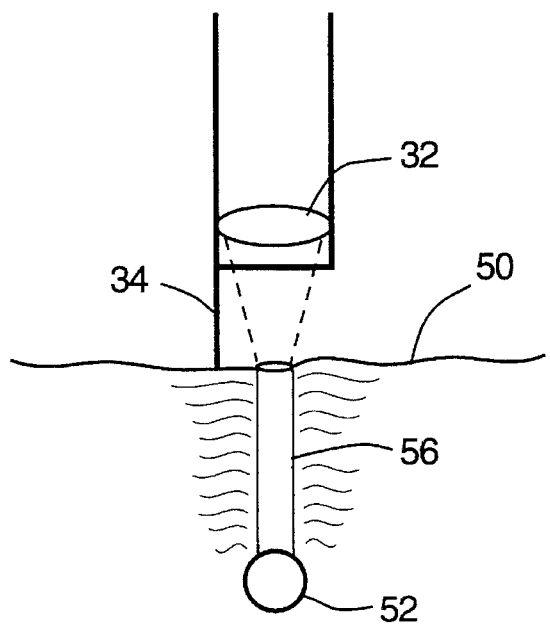
FIG. 2 is a sectional view illustrating the treatment of a vessel in accordance with the subject invention.

A delivery handpiece 30 is mounted at the end of the articulated arm. For the method of the subject invention, a conventional fine focus handpiece was selected. The fine focus handpiece includes a lens 32 for creating a small diameter spot in the focal plane of the lens. As seen in FIG. 2, a spacer bar 34 is mounted at the end of the handpiece 30. The bar 34 permits the surgeon to readily space the end of the handpiece from the tissue an amount which insures a sharply focused beam on the tissue surface 50.

In accordance with the method of the subject invention, the handpiece is placed on the surface of the skin 50, above the vessel 52 to be treated. The laser 20 is then energized in a manner to ablate the tissue below the focused beam. As noted above, each pulse will remove a fixed volume of tissue. Repeated pulses will successively deepen the hole. The number of pulses delivered at each spot will be a function of the power and energy settings on the laser and the depth of the vessel beneath the skin.

Using a fine focus handpiece, a hole 56 is drilled into the tissue. In initial experiments, a handpiece designed to produce a 0.2 mm spot size was used. It is believed that a handpiece capable of providing a spot size of 0.1 mm would also be useful in certain situations. Pulse energies of 250 millijoules were used. The laser was set to generate pulses at a frequency of 20 Hz (5 watts average power.) The laser was also set to generate a pulse burst having a length of 200 milliseconds which would produce about four pulses for each activation of a foot switch. It was found that two to four such pulse bursts were necessary to drill down to a typical vein 50 which could lie up to 5 mm below surface.

In accordance with the subject invention, the hole 56 is drilled through the skin and into the vessel. Once the vessel is pierced, the blood will be heated, causing the vessel to coagulate and collapse at that site.

Figure 3:
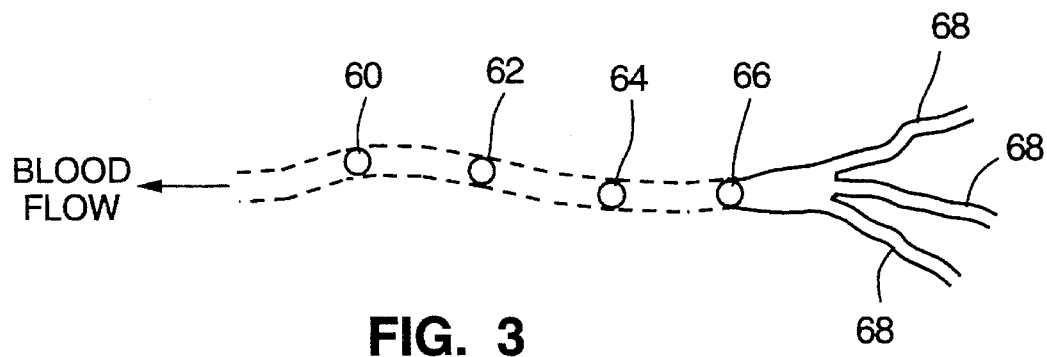
FIG. 3 is a top view illustrating a pattern of sites used to treat a vessel.

In order to collapse a long length of the vein, multiple treatment sites are necessary. As seen in FIG. 3, it is desirable to locate the first treatment site 60 at an downstream point with respect to the flow of blood in the vessel. The surgeon can then sequentially drill holes into the vessel at multiple sites (62, 64, 66) upstream from the first site 60. In initial experiments, the spacing between the sites was 1 to 5 cm.

The reason for beginning treatment of the vein at a downstream point with respect to the blood flow is twofold. First, in order to get the best long term results, it is necessary to treat each vein at multiple sites. If an upstream point in the vein is treated first, the downstream section of the vein will immediately collapse making finding and treating additional downstream sections of the vein more difficult. Secondly, if the larger downstream sections of the vein are treated first, the need to treat the smaller upstream tributary branches 68 can be reduced.

It has also been found the collapse of the vein can be aided by applying compression immediately after laser treatment. Compression on the treatment site should be maintained for a few minutes.

Although the subject method requires drilling into the skin, it does have some significant advantages when compared to prior laser treatment systems where the surface of the skin is irradiated and heated. For example, since the laser energy is narrowly channeled and does not diffuse outwardly, the amount of thermal damage to the tissue surrounding the holes is substantially lessened. In addition, since the drilled holes have a very small diameter, the chances of scarring and coloration changes are minimized.

While the subject invention has been described with reference to a preferred embodiment, various changes and modifications could be made therein, by one skilled in the art, without varying from the scope and spirit of the subject invention as defined by the appended claims.

I claim:

1. A method of treating an elongated blood vessel located in the tissue under the surface of the skin comprising the steps of:

irradiating a spot on the surface of the skin with laser light having a diameter less than 0.2 mm and a fluence and power sufficient to ablate a hole in the tissue having a depth which reaches the vessel causing the vessel to bleed and coagulate; and repeating the irradiating step at multiple spots on the skin along the length of the vessel to be treated.

2. A method as recited in claim 1 wherein the step of irradiating is performed with a far infrared laser radiation.

3. A method as recited in claim 1 wherein said step of irradiating is performed with laser from a carbon dioxide laser.

4. A method as recited in claim 3 wherein said each spot is irradiated with pulses of laser light, wherein each pulse has a duration less than one millisecond.

5. A method as recited in claim 4 wherein each pulse has an energy between 100 and 500 millijoules.

6. A method as recited in claim 1 wherein the spot on the surface of the skin has a diameter of 0.1 mm.

7. A method as recited in claim 1 wherein the spots are spaced apart by about 1 to 5 cm.

\* \* \* \* \*